United States Patent [19]

Kasamatsu et al.

[11] 4,443,438

[45] Apr. 17, 1984

[54] INSECTICIDAL AND/OR ACARICIDAL COMPOSITION EXHIBITING LOW TOXICITY TO MAMMALS AND FISH

[75] Inventors: Kiyoshi Kasamatsu, Takarazuka; Masachika Hirano, Ibaraki; Takeshi Okuno, Tokyo, all of Japan

[73] Assignee: Sumitomo Chemical Company, Limited, Osaka, Japan

[21] Appl. No.: 406,014

[22] Filed: Aug. 6, 1982

Related U.S. Application Data

[62] Division of Ser. No. 99,482, Dec. 3, 1979, Pat. No. 4,357,348.

[30] Foreign Application Priority Data

Dec. 8, 1978 [JP] Japan .................. 53-152289
Dec. 8, 1978 [JP] Japan .................. 53-152290

[51] Int. Cl.³ .............. A01N 57/00; A01N 37/34; A01N 57/26
[52] U.S. Cl. .............. 424/200; 424/304
[58] Field of Search .............. 424/200, 304

[56] References Cited

U.S. PATENT DOCUMENTS

| | | | |
|---|---|---|---|
| 3,666,789 | 5/1972 | Itaya et al. | 424/305 |
| 3,835,176 | 9/1974 | Matsuo et al. | 424/306 |
| 4,301,155 | 11/1981 | Larson | 424/200 |
| 4,325,948 | 4/1982 | Maurer et al. | 424/200 |
| 4,341,760 | 7/1982 | Matthewson | 424/200 |
| 4,362,722 | 12/1982 | Stubbs | 424/200 |

FOREIGN PATENT DOCUMENTS

| | | | |
|---|---|---|---|
| 2757768 | 6/1978 | Fed. Rep. of Germany | 424/304 |
| 77/3861 | 6/1977 | South Africa | 424/200 |

*Primary Examiner*—Douglas W. Robinson

*Attorney, Agent, or Firm*—Stevens, Davis, Miller & Mosher

[57] ABSTRACT

The present invention relates to insecticidal compositions of low toxicity to fishes and mammals characterized by containing m-(p-bromophenoxy)-α-cyanolbenzyl trans- or trans-rich-2,2-dimethyl-3-(2,2-dichlorovinyl)cyclopropanecarboxylate of the formula (I),

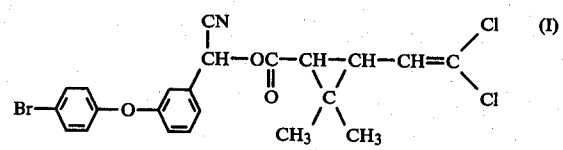

and at least one of the organo-phosphoric esters of the formula (II),

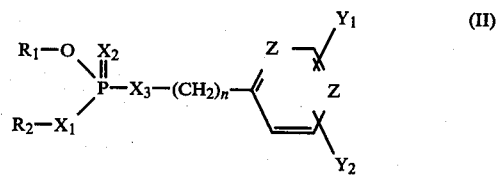

wherein $R_1$ and $R_2$ are each a $C_1$-$C_3$ alkyl group, $X_1$, $X_2$ and $X_3$ are each an oxygen or sulfur atom, $Y_1$ and $Y_2$, which may be the same or different, are each a $C_1$-$C_3$ lower alkyl, methylmercapto, cyano or nitro group or a halogen atom, Z is a carbon or nitrogen atom and n is 0 or 1, in a ratio of 1 to 1–100 (part by weight) of the former to the latter, and insecticides obtained by mixing said compositions with a carrier or a diluent and if necessary an additive. The term "trans-rich" shows the ratio of trans/cis is not less than 75/25.

8 Claims, No Drawings

INSECTICIDAL AND/OR ACARICIDAL COMPOSITION EXHIBITING LOW TOXICITY TO MAMMALS AND FISH

This is a division of application Ser. No. 99,482 filed Dec. 3, 1979, now U.S. Pat. No. 4,357,348.

The present invention relates to insecticidal compositions of low toxicity to fishes and mammals. More particularly, it relates to insecticidal compositions of low toxicity to fishes and mammals characterized by containing m-(p-bromophenoxy)-α-cyanolbenzyl trans- or trans-rich-2,2-dimethyl-3-(2,2-dichlorovinyl)cyclopropanecarboxylate of the formula (I),

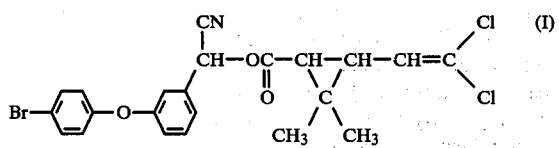

and at least one of the organo-phosphoric esters of the formula (II),

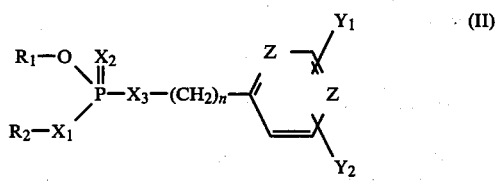

wherein $R_1$ and $R_2$ are each a $C_1$–$C_3$ alkyl group, $X_1$, $X_2$ and $X_3$ are each an oxygen or sulfur atom, $Y_1$ and $Y_2$, which may be the same or different, are each a $C_1$–$C_3$ lower alkyl, methylmercapto, cyano or nitro group or a halogen atom, Z is a carbon or nitrogen atom and n is 0 or 1, and/or the carbamic esters of the formula (III),

wherein R is a group of the formula,

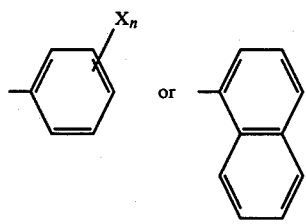

in which X is a $C_1$–$C_4$ alkyl or $C_1$–$C_4$ alkoxyl group and n is 1 or 2, in a ratio of 1 to 1–100 (part by weight) of the former to the latter, and insecticides obtained by mixing said compositions with a carrier or a diluent and if necessary an additive. The term "trans-rich" shows the ratio of trans/cis is not less than 75/25.

Exterminating agents against harmful organisms are essential materials for controlling diseases and insects doing damage to agricultural crops, thereby maintaining high levels of agricultural production. Extermination of insects and mites carrying infectious pathogens is very effective for preventing diseases from spreading, and for this purpose the use of insecticides and acaricides is most effective.

In recent years, however, organo-chlorine insecticides such as BHC and DDT have become markedly limited in use, because they generated insects resistant thereto and caused various problems such as environmental pollution and toxicity to organisms out of target.

Generation of resistant insects is also observed in the fields wherein organo-phosphate or carbamate insecticides are used. This makes it necessary to apply large amounts of pesticides, which becomes a serious problem in terms of toxicity to fishes and mammals. At present, development of various synthetic pyrethroid compounds are studied as substitutes for these insecticides, and some of the compounds are now in practical use. But, as is shown in the literature: J. Miyamoto, Environmental Health Perspectives Vol. 14, 15 (1976), pyrethroid insecticides generally exhibit a strong toxicity to fishes. By this property of the pyrethroid insecticides, it is meant that there is a danger of fishes being exterminated when the pyrethroids are applied to control insects in paddy fields, or aquatic insects such as mosquito larvae and gnat larvae, or when applied by air over a wide area wherein lakes, ponds and rivers are present. Since such application as this occupies a large proportion of all the applications of insecticides, the high toxicity to fishes of common pyrethroid compounds is a serious problem which should be improved in order to use the compounds for insect extermination.

For the reasons as described above, the inventors extensively studied to overcome the foregoing drawbacks of the insecticides, and as a result, it was unexpectedly found that compositions containing the compound of the formula (I) and at least one of organo-phosphoric esters of the formula (II) and/or carbamic esters of the formula (III) in a ratio of 1 to 1–100 (part by weight) of the former to the latter, have excellent characteristics such as a strong insecticidal activity and a low toxicity to fishes and mammals. The inventors thus attained the present invention.

The compositions of the present invention exhibit a particularly strong controlling effect against green rice leafhoppers which have acquired increased resistance to organo-phosphate and carbamate insecticides, and also their controlling effect against other insects is high. Further, they have a characteristic of low toxicity to fishes and mammals, so that they are suitable for exterminating aquatic insects living in paddy fields, ponds, lakes, rivers and woods and forests.

It is reported in Published Unexamined Japanese Patent Application No. 125145/1977 that one component of the present compositions, the compound of the formula (I), has insecticidal and acaricidal activity. It is also well known that organo-phosphoric esters have insecticidal and fungicidal activity. But, as clearly shown by the experimental examples described hereinafter, mixtures of the both have an activity which is far stronger than expected from the activity of each component. Consequently, the compositions of the present invention have a very remarkable synergistic effect.

As described above, the object of the present invention is to develop pesticides of low toxicity to fishes suitable for exterminating aquatic insects living in paddy fields, ponds, lakes, rivers and woods and forests, and therefore if the toxicity to fishes and mammals of said mixtures becomes also as great as the remarkable increase of insect-controlling effects, said mixtures may not be said to be in a high technical level in terms of practical value.

Surprisingly, however, the compositions of the present invention containing the compound of the formula (I) and at least one of organo-phosphoric esters of the formula (II) and/or carbamic esters of the formula (III) in a ratio of 1 to 1–100 (part by weight) of the isomer to the latter, exhibit a synergistically increased controlling effect against harmful organisms, as described above, but their toxicity to fishes (e.g. carps, killifishes) and mammals (e.g. mice, rats) is within the sum of the toxicity of each component or markedly lower than the sum. Consequently, the compositions of the present invention are of a great significance in performing the extermination of aquatic insects living in paddy fields, ponds, lakes, rivers and woods and forests.

As the organo-phosphoric esters of the formula (II), the following compounds are given as typical examples:

O,O-Dimethyl O-(3-methyl-4-nitrophenyl)phosphorothioate (Sumithion)

O,O-Dimethyl O-[3-methyl-4-(methylthio)phenyl]thiophosphate (Baycid)

O,O-Diethyl O-(2-isopropyl-4-methyl-6-pyrimidinyl)phosphorothioate (Diazinon)

O,O-Dimethyl O-4-cyanophenylphosphorothioate (Cyanox)

O,O-Di-n-propyl p-methylthiophenylphosphate (Kayaphos)

O,O-Diisopropyl S-benzylphosphorothioate (IBP)

As the carbamic esters of the formula (III), the following compounds are given as typical examples:

1-Naphthyl N-methylcarbamate (NAC)
3,4-Xylyl N-methylcarbamate (MPMC)
m-Tolyl N-methylcarbamate (MTMC)
2-sec-Butylphenyl N-methylcarbamate (BPMC)
2-Isopropoxyphenyl N-methylcarbamate (PHC)
m-Isopropylphenoxy N-methylcarbamate (MIPC)

Compositions containing the compound of the formula (I) and at least one of the organo-phosphoric esters of the formula (II) and/or carbamic esters of the formula (III) can be formulated into any one of the preparation forms such as dusts, wettable powders, granules, fine granules, oil sprays and baits by mixing with one or more of carriers or diluents and if necessary one or more of additives. As the carriers or diluents, there may be mentioned diatomaceous earth, white carbon, talc, Fubasami Clay, GSM Clay (a registered trade mark of Zieklite Mining Co.), acid clay, bentonite, Tokusil Gu-N (a registered trade mark of Tokuyama Soda Co.), sericite, calcium carbonate, Carplex #80 (a registered trade mark of Shionogi Seiyaku Co.), calcium lignosulfonate, San-X P201 (a registered trade mark of Sanyo Kokusaku Pulp Co.), kerosene, xylene, cyclohexanone, n-hexane, Isopar M (a registered trade mark of ESSO Standard Petroleum Co.), Solvesso 150 (a registered trade mark of ESSO Standard Petroleum Co.), Kawakasol (a registered trade mark of Kawasaki Kasei Co.), freon gas and the like. As the addition, there may be mentioned Sorpol SM-200, Sorpol 3005X, Sorpol 2020, Sorpol 2680, Sorpol 2495G, Sorpol 5029-0, Sorpol 5060, Sorpol SM-100S (all Sorpols are registered trade marks of Toho Kagaku Co.), Hymal PS-90A, Hymal PS-10A, Hymal Co (all Hymals are registered trade marks of Matsumoto Yushi Co.), Toxanon PW-S46 (a registered trade mark of Sanyo Kasei Co.), Atmos 300 (a registered trade mark of Atlas Kagaku Kogyo Co.), Toyolignin CT (a registered trade mark of Toyo Spinning Co.), isopropyl acid phosphate (hereinafter referred to as PAP), α-[2-(2-butoxyethoxy)ethoxy]-4,5-methylenedioxy-2-propyltoluene (hereinafter referred to as piperonylbutoxide), 1,2-methylenedioxy-4-[2-(octylsulfinyl)propyl]benzene (hereinafter referred to as sulfoxide), 4-(3,4-methylenedioxyphenyl)-5-methyl-1,3-dioxane (hereinafter referred to as sufroxane), N-(2-ethylhexyl)bicyclo[2,2,1]hepta-5-ene-2,3-dicarboximide (hereinafter referred to as MGK-264), octachlorodipropyl ester (hereinafter referred to as S-421), isobornyl thiocyanoacetate (hereinafter referred to as Thanite), 2,6-di-tert-butyl-4-methylphenol (hereinafter referred to as BHT), a mixture of 2-tert-butyl-4-methoxyphenol and 3-tert-butyl-4-methoxyphenyl (hereinafter referred to as BHA) and the like.

The content of the active ingredient in the present insecticidal compositions is preferably within a range of 0.01% to 80%, more preferably 0.05% to 50%. The ratio of compound (I) to organophosphoric ester (II) or carbamic ester (III) of the active ingredient is preferably 1 part by weight of 1–100 parts by weight. More particularly, the ratio is preferably 1 part by weight to 20–100 parts by weight for dusts, and 1 part by weight of 2–30 parts by weight for other preparation forms.

Next, specific examples of insect which can effectively be controlled by the present compositions will be given.

1. Hemiptera

For example green rice leafhopper (*Nephotettix cincticeps*), green leafhopper (*Tettigella viridis*), zigzag-striped leafhopper (*Inazuma dorsalis*), white-backed planthopper (*Sogatella furcifera*), brown planthopper (*Nilaparvata lugens*), smaller brown planthopper (*Laodelphax striatellus*), grain aphid (*Rhopalosiphum padi*), common green stink bug (*Nezara antennata*), white-spotted bug (*Eysarcaris ventralis*), Togo hemipterus, narrow rice bug (*Leptocorixa variconis*), comstock mealy bug (*Pseudococcus comstoki*).

2. Lepidoptera

For example rice stem borer (*Chilo suppressalis*), grass leaf roller (*Cnaphalocrocis medinalis*), pine caterpillar (*Dendrolimus spectabilis*), tent caterpillar (*Malacosoma neustria*), rice-plant skipper (*Parnara guttata*), spruce bud worm (*Choristoneura fumiferana*).

3. Coleoptera

For example rice leaf beetle (*Oulema oryzae*), rice plant weevil (*Echinocoemus squameus*), cupreons chafer (*Anomala cuprea*), rice plant weevil (*Echinocnemus squameus*), Japanese pine sawyer (*Monochamus alternatus*).

4. Diptera

For example yellow fever mosquito (*Aedes aegypti*), northern house mosquito (*Culex pipiens pallens*), malaria mosquito (*Anopheles stephansi*), gnats, midges, housefly (*Musca domestica*), sarcophagid fly (*Sarcophaga* spp.), rice leaf miner (*Agromyza oryzae*).

5. Orthoptera

For example short-winged rice (*Oxya yezoensis*), locusts

6. Isoptera

For example Formosan termite (*Copotermes formosanus*), Japanese termite (*Leucotermes speratus*).

7. Dictyoptera

For example German cockroach (*Blattela germanica*), smoky brown cockroach (*Periplaneta fuliginosa*), American cockroach (*Periplaneta americana*).

8. Acarina

For example carmine mite (*Tetranychus cinnabarinus*), two-spotted spider mite (*Tetranychus urticae*), sugi spider mite (*Oligonychus hondoensis*), citrus red mite (*Panonychus citri*), European red mite (*Panonychus ulmi*), cyclamen mite (*Steneotarsonemus pallidus*).

In order to make it clear that the compositions of the present invention have an excellent insecticidal activity as well as a low toxicity to fishes and warm-blooded animals, a detailed explanation will be given with reference to the following preparation examples and experimental examples, but the present invention is not of course limited to these examples.

All parts in the preparation examples and experimental examples are by weight.

Preparation example 1—Wettable powder

The compound of the formula (I), the organophosphoric ester and/or the carbamic ester and Sorpol shown in the following table are well mixed in the proportion shown in the table, and diatomaceous earth and white carbon of the proportion shown in the table are added thereto. The mixture is well mixed with stirring to obtain a wettable powder of each compound.

TABLE 1

| No. of wettable powder | Compound (1) of this invention | Organophosphorus insecticides | Carbamate insecticides | Sorpol | Diatomaceous earth | White carbon |
|---|---|---|---|---|---|---|
| (1) | dl(acid moiety)-trans, 5 parts | Sumithion 25 parts | — | 2495G 2 parts | 58 parts | 10 parts |
| (2) | dl(acid moiety)-trans, 5 parts | Baycid 25 parts | — | 5029-0 " | " | " |
| (3) | dl(acid moiety)-trans, 5 parts | IBP 25 parts | — | 2495G " | " | " |
| (4) | dl(acid moiety)-trans, 2 parts | — | MPMC 25 parts | 5029-0 " | 71 parts | — |
| (5) | dl(acid moiety)-trans, 2 parts | — | MTMC " | " " | " | — |
| (6) | dl(acid moiety)-trans, 2 parts | — | BPMC " | " " | " | — |
| (7) | dl(acid moiety)-trans, 2 parts | Sumithion 10 parts | BPMC 10 parts | " " | 66 parts | 10 parts |
| (8) | dl(acid moiety)-cis, trans(cis/trans = 23/77), 5 parts | Sumithiuon 25 parts | — | 2495G " | 58 parts | " |
| (9) | dl(acid moiety)-cis, trans(cis/trans = 23/77), 5 parts | Baycid 25 parts | — | 5029-0 " | " | " |
| (10) | dl(acid moiety)-cis, trans(cis/trans = 23/77), 5 parts | IBP 25 parts | — | 2495G " | " | " |
| (11) | dl(acid moiety)-cis, trans(cis/trans = 23/77), 2 parts | — | NAC 25 parts | 5029-0 " | 71 parts | — |
| (12) | dl(acid moiety)-cis, trans(cis/trans = 23/77), 2 parts | — | MPMC 25 parts | " " | " | — |
| (13) | dl(acid moiety)-cis, trans(cis/trans = 23/77), 2 parts | — | MTMC 25 parts | " " | " | — |
| (14) | dl(acid moiety)-cis,trans(cis/trans = 23/77), 2 parts | — | BPMC 25 parts | " " | " | 10 parts |
| (15) | dl(acid moiety)-cis, trans(cis/trans = 23/77), 2 parts | Sumithion 10 parts | BPMC 10 parts | " " | 66 parts | " |
| (16) | dl(acid moiety)-cis, trans(cis/trans = 23/77), 2 parts | Sumithion 10 parts | MPMC 10 parts | " " | " | " |
| (17) | dl(acid moiety)-cis, trans(cis/trans = 23/77), 2 parts | Sumithion 45 parts | — | 2495G 2 parts | 41 parts | " |
| (18) | dl(acid moiety)-cis, trans(cis/trans = 23/77), 2 parts | Baycid 45 parts | — | 5029-0 2 parts | " | " |
| (19) | dl/acid moiety)- | IBP 45 parts | — | 2495G 2 parts | " | " |

TABLE 1-continued

| No. of wettable powder | Compound (1) of this invention | Organo-phosphorus insecticides | Carbamate insecticides | Sorpol | Diatomo-ceous earth | White carbon |
|---|---|---|---|---|---|---|
| | cis, trans(cis/trans = 23/77), 2 parts | | | | | |

Preparation example 2–Dust

The compound of the formula (I), the organophosphoric ester and/or the carbamic ester shown in the following table are dissolved in acetone, and PAP (described above), Fubasami Clay and, if necessary, white carbon are added thereto. The mixture is well mixed with stirring, and acetone is removed by evaporation to obtain a dust of each compound.

TABLE 2

| No. of Dust | Compound (1) of this invention | Organophosphorus insecticides | Carbamate insecticides | PAP | Clay | White carbon |
|---|---|---|---|---|---|---|
| (1) | dl(acid moiety)-trans, 0.1 part | Sumithion 3 parts | — | 0.2 part | 94.7 parts | 2 parts |
| (2) | dl(acid moiety)-trans, 0.1 part | Baycid 3 parts | — | " | " | " |
| (3) | dl(acid moiety)-trans, 0.1 part | Diazinon 3 parts | — | " | " | " |
| (4) | dl(acid moiety)-trans, 0.1 part | Cyanox 3 parts | — | " | " | " |
| (5) | dl(acid moiety)-trans, 0.1 part | Kayaphos 3 parts | — | " | " | " |
| (6) | dl(acid moiety)-trans, 0.1 part | IBP 3 parts | — | " | " | " |
| (7) | dl(acid moiety)-trans, 0.1 part | — | NAC 3 parts | " | 96.7 parts | — |
| (8) | dl(acid moiety)-trans, 0.1 part | — | MPMC 3 parts | " | " | — |
| (9) | dl(acid moiety)-trans, 0.1 part | — | MTMC 3 parts | " | " | — |
| (10) | dl(acid moiety)-trans, 0.1 part | — | BPMC 3 parts | " | " | — |
| (11) | dl(acid moiety)-trans, 0.1 part | — | PHC 3 parts | " | " | — |
| (12) | dl(acid moiety)-trans, 0.1 part | — | MIPC 3 parts | " | " | — |
| (13) | dl(acid moiety)-trans, 0.1 part | Sumithion 3 parts | BPMC 2 parts | " | 92.7 parts | 2 parts |
| (14) | dl(acid moiety)-trans, 0.1 part | Sumithion 3 parts | MPMC 2 parts | " | " | " |
| (15) | dl(acid moiety)-cis, trans(cis/trans = 23/77), 0.1 part | Sumithion 3 parts | — | " | 94.7 parts | " |
| (16) | dl(acid moiety)-cis, trans(cis/trans = 23/77), 0.1 part | Baycid 3 parts | — | " | " | " |
| (17) | dl(acid moiety)-cis, trans(cis/trans = 23/77), 0.1 part | Diazinon 3 parts | — | " | " | " |
| (18) | dl(acid moiety)-cis, trans(cis/trans = 23/77), 0.1 part | Kayaphos 3 parts | — | " | " | " |
| (19) | dl(acid moiety)-cis, trans(cis/trans = 23/77), 0.1 part | IBP 3 parts | — | " | " | " |
| (20) | dl(acid moiety)-cis, trans(cis/trans = 23/77), 0.1 part | — | NAC 3 parts | " | 96.7 parts | — |
| (21) | dl(acid moiety)-cis, trans(cis/trans = 23/77), 0.1 part | — | MPMC 3 parts | " | " | — |
| (22) | dl(acid moiety)-cis, trans(cis/trans = 23/77), 0.1 part | — | MTMC 3 parts | " | " | — |
| (23) | dl(acid moiety)-cis, trans(cis/ | — | BPMC 3 parts | " | " | — |

TABLE 2-continued

| No. of Dust | Compound (1) of this invention | Organophosphorus insecticides | Carbamate insecticides | PAP | Clay | White carbon |
|---|---|---|---|---|---|---|
| | trans = 23/77), 0.1 part | | | | | |
| (24) | dl(acid moiety)-cis, trans(cis/trans = 23/77), 0.1 part | — | PHC 3 parts | " | " | — |
| (25) | dl(acid moiety)-cis, trans(cis/trans = 23/77), 0.1 part | — | MIPC 3 parts | " | " | — |
| (26) | dl(acid moiety)-cis, trans(cis/trans = 23/77), 0.1 part | Sumithion 3 parts | BPMC 2 parts | " | 92.7 parts | 2 parts |
| (27) | dl(acid moiety)-cis, trans(cis/trans = 23/77), 0.1 part | Sumithion 3 parts | MPMC 2 parts | " | " | " |
| (28) | dl(acid moiety)-cis, trans(cis/trans = 23/77), 0.1 part | — | NAC 1 part | " | 98.7 parts | — |
| (29) | dl(acid moiety)-cis, trans(cis/trans = 23/77), 0.1 part | — | MPMC 1 part | " | " | — |
| (30) | dl(acid moiety)-cis, trans(cis/trans = 23/77), 0.1 part | — | MTMC 1 part | " | " | — |
| (31) | dl(acid moiety)-cis, trans(cis/trans = 23/77), 0.1 part | — | BPMC 1 part | " | " | — |
| (32) | dl(acid moiety)-trans, 0.05 part | IBP 2 parts | — | " | 95.75 parts | 2 parts |
| (33) | dl(acid moiety)-trans, 0.05 part | — | MPMC 1.5 parts | " | " | " |
| (34) | dl(acidmoiety)-trans, 0.05 part | — | BPMC 1.5 parts | " | " | " |
| (35) | dl(acid moiety)-trans, 0.05 part | — | MTMC 1.5 parts | " | " | " |
| (36) | dl(acid moiety)-cis, trans(cis/trans = 23/77), 0.05 part | Sumithion 2 parts | — | " | " | " |
| (37) | dl(acid moiety)-cis, trans(cis/trans = 23/77), 0.05 part | Baycid 2 parts | — | " | " | " |
| (38) | dl(acid moiety)-cis, trans(cis/trans = 23/77), 0.05 part | Diazinon 2 parts | — | " | " | " |
| (39) | dl(acid moiety)-cis, trans(cis/trans = 23/77), 0.05 part | Kayaphos 2 parts | — | " | " | " |
| (40) | dl(acid moiety)-cis, trans(cis/trans = 23/77), 0.05 part | IBP 2 parts | — | " | " | " |
| (41) | dl(acid moiety)-cis, trans(cis/trans = 23/77), 0.05 part | — | NAC 1.5 parts | " | 96.25 parts | " |
| (42) | dl(acid moiety)-cis, trans(cis/trans = 23/77), 0.05 part | — | MPMC 1.5 parts | " | " | " |
| (43) | dl(acid moiety)-cis, trans(cis/trans = 23/77), 0.5 part | — | MTMC 1.5 parts | " | " | " |
| (44) | dl(acid moiety)-cis, trans(cis/trans = 23/77), 0.05 part | — | BPMC 1.5 parts | " | " | " |
| (45) | dl(acid moiety)- | — | PHC 1.5 parts | " | " | " |

TABLE 2-continued

| No. of Dust | Compound (1) of this invention | Organophosphorus insecticides | Carbamate insecticides | PAP | Clay | White carbon |
|---|---|---|---|---|---|---|
| | cis, trans(cis/trans = 23/77), 0.05 part | | | | | |
| (46) | dl(acid moiety)-cis, trans(cis/trans = 23/77), 0.05 part | — | MIPC 1.5 parts | " | " | " |
| (47) | dl(acid moiety)-cis, trans(cis/trans = 23/77), 0.05 part | Sumithion 2 parts | BPMC 1.5 parts | " | 94.25 parts | " |
| (48) | dl(acid moiety)-cis, trans(cis/trans = 23/77), 0.05 part | Sumithion 2 parts | MPMC 1.5 parts | " | " | " |

Preparation example 3—Granule

To a mixture of 1 part of the present compound of the formula (I) [dl(acid moiety)-cis,trans isomer (cis/trans=25/75)] and 4 parts of Diazinon are added 5 parts by Toyolignin CT, 2 parts of Sorpol 5060 and 88 parts of Fubasami Clay, and the mixture is well mixed while being stirred in a mortar. Thereafter, to the mixture is added water in an amount of 10% by weight based thereon, and the mixture is well mixed with stirring, granulated by means of a granulator and air-dried to obtain a granule.

Preparation example 4—Fine granule

To 0.2 part of each of the compounds represented by the formula (I) [dl(acid moiety)-cis,trans isomers (cis/trans=23/77)] are added 2 or 5 parts of one of Sumithion, Baycid, Diazinon and Kayaphos, and 5 parts of Toyolignin CT. The mixture is then made up to 100 parts with addition of Fubasami Clay. The resulting mixture is well mixed while being stirred in a mortar, and water in an amount of 10% by weight based on the mixture is added thereto. The mixture is then granulated by means of a granulator for fine granule production and air-dried to obtain a fine granule of each mixture of the active ingredients.

Preparation example 5—Fine granule

To 0.2 part of each of the compounds represented by the formula (I) [dl(acid moiety)-cis,trans isomers (cis/trans=23/77)] are added 2 or 5 parts of one of NAC, MPMC and BPMC, and 5 parts of Toyolignin CT. The mixture is then made up to 100 parts with addition of Fubasami Clay. The resulting mixture is well mixed while being stirred in a mortar, and water in an amount of 10% by weight based on the mixture is added thereto. The mixture is then granulated by means of a granulator for fine granule production and air-dried to obtain a fine granule of each mixture of the active ingredients.

Preparation example 5—Oil spray 0.02 Part by the compound of the formula (I) [dl(acid moiety)-cis,trans isomer (cis/trans=23/77)] and 0.05 part of Sumithion are mixed. The mixture is dissolved in kerosene and made up to 100 parts with kerosene to obtain an oil spray.

Next, explanation will be given regarding the insecticidal activity and toxicity to fishes of the mixed insecticidal compositions of the present invention thus obtained.

Experimental example 1

The dusts (1), (15), (17), (26), (28) or (29) prepared in Preparation example 2 were each applied, at a rate of 3 kg/10 are, to paddy field divided into portions having the same area of 6.6 m × 10 m wherein green rice leafhoppers (Nephotettix cincticeps) in the fourth period of occurrence were liberated. The density of green rice leafhopper adults was examined at predetermined periods by the sweeping method to obtain the density index.

$$\text{Density index} = \frac{C_b \times T_a}{C_a \times T_b} \times 100$$

$C_a$: number of insects in untreated plot after application.
$C_b$: number of insects in untreated plot before application.
$T_a$: number of insects in treated plot after application.
$T_b$: number of insects in treated plot before application.

TABLE 3

| | Density index | |
|---|---|---|
| Test pesticide | After 2 days | After 15 days |
| Dust (1) | 0 | 12 |
| Dust (15) | 2 | 17 |
| Dust (17) | 1 | 11 |
| Dust (26) | 0 | 8 |
| Dust (28) | 2 | 15 |
| Dust (29) | 0 | 10 |
| Compound of the formula (I) [dl(acid moiety)-trans isomer: as 0.1% dust | 3 | 18 |
| Compound of the formula (I) [dl(acid moiety)-cis, trans isomer (cis/trans = 23/77)]: as 0.1% dust | 5 | 25 |
| Sumithion: as 5% dust | 60 | 95 |
| Diazinon: as 5% dust | 20 | 35 |
| NAC: as 3% dust | 10 | 43 |
| MPMC: as 3% dust | 7 | 60 |
| Untreated | 100 | 100 |

Experimental example 2

The wettable powders (11), (12), (14), (17), (18) or (19) prepared in Preparation example 1 were each diluted 2,500 times with water. The dilute solution was sprayed on rice plants in a 180-ml plastic cup at a rate of 15 cc/3 cups by means of a turn table. After air-drying, the treated rice plants were placed in a 5-liter beaker which was then covered with gauze. About 15 female adults of pesticide-resistant green rice leafhopper (*Nephotettix cincticeps*) were released in the beaker. After 3 hours, the knock-down ratio was examined, and after 24 hours the mortality was examined.

TABLE 4

| Test pesticide | Rate of dilution (time) | Knock-down ratio (%) after 3 hours | Mortality (%) after 24 hours |
| --- | --- | --- | --- |
| Wettable powder (11) | 2,500 | 60 | 100 |
| Wettable powder (12) | 2,500 | 63 | 100 |
| Wettable powder (14) | 2,500 | 53 | 100 |
| Wettable powder (17) | 2,500 | 57 | 100 |
| Wettable powder (18) | 2,500 | 67 | 100 |
| Wettable powder (19) | 2,500 | 67 | 100 |
| Compound of the formula (I) [dl(acid moiety)-cis, trans isomer (cis/trans = 50/50)]: as 20% wettable powder | 25,000 | 50 | 80 |
| Sumithion: as 45% wettable powder | 2,000 | 0 | 15 |
| Baycid: as 45% wettable powder | 2,000 | 0 | 20 |
| IBP: as 45% wettable powder | 2,000 | 0 | 0 |
| NAC: 25% wettable powder | 2,000 | 5 | 10 |
| MPMC: 25% wettable powder | 2,000 | 10 | 10 |
| BPMC: 25% wettable powder | 2,000 | 3 | 3 |
| Untreated | — | 0 | 0 |

As is apparent from Table 4, it was found that the compositions of the present invention show a remarkable synergistic effect in the knock-down activity and insecticidal activity against resistant green rice leafhoppers.

Experimental example 3

The dusts (36), (37), (39), (43), (47) or (48) prepared in Preparation example 2 were each applied by means of a Bell jar duster to rice plants in a 1/10,000 are Wagner's pot at a rate of 2 kg/10 are. The treated pot was placed in a cylinder (diameter 20 cm, height 60 cm) which was then covered with gauze. About 30 female adults of pesticide-resistant green rice leafhopper (*Nephotettix cincticeps*) were liberated therein. After 24 hours, the mortality was examined.

TABLE 5

| Test pesticide | Mortality (%) after 24 hours |
| --- | --- |
| Dust (36) | 100 |
| Dust (37) | 100 |
| Dust (39) | 100 |
| Dust (43) | 100 |
| Dust (47) | 100 |
| Dust (48) | 100 |
| Compound of the formula (I) [dl(acid moiety)-cis, trans isomer (cis/trans = 23/77)]: as 0.05% dust | 85 |
| Sumithion: as 2% dust | 10 |
| Baycid: as 2% dust | |
| Kayaphos: as 2% dust | 43 |
| MTMC: as 2% dust | 30 |
| Sumithion (2%) + BPMC (1.5%): as dust | 43 |
| Sumithion (2%) + MPMC (1.5%): as dust | 47 |

TABLE 5-continued

| Test pesticide | Mortality (%) after 24 hours |
| --- | --- |
| Untreated | 0 |

Experimental example 4

About 50 eggs just before hatch of rice stem borer (*Chilo suppressalis*) were put on rice plants at the tiller stage cultivated in a 1/5,000 are Wagner's pot. After 5 days, the dust (1) prepared in Preparation example 2 was applied thereto at a rate of 3 kg/10are by means of a Bell jar duster. Five days after application, the rice stem was dissected to observe the dead and alive of rice stem borers.

TABLE 6

| Test pesticide | Mortality (%) |
| --- | --- |
| Dust (1) | 100 |
| Compound of the formula (I) [dl(acid moiety)-trans isomer]: as 0.1% dust | 20 |
| Sumithion: as 3% dust | 70 |

Experimental example 5

The dusts (1), (2), (3), (4), (5), (7), (8), (11), (12), (13), (14), (15), (26) and (27) prepared in Preparation example 2 were each applied, by means of a Bell jar duster, to rice plants at the tiller stage cultivated in a 1/5,000 are Wagner's pot at a rate of 3 kg/10 are. The rice plant was covered with a wirescreen cage and 30 smaller brown planthopper adults (*Laodelphax striatellus*) were liberated in the cage. After 24 hours, 100% of the adults could be killed in any case.

Experimental example 6

The dusts (3), (6), (7), (11) and (12) prepared in Preparation example 2 were each diluted with dechlorinated city water to the pre-determined concentration of the active ingredient. Ten liters of the dilute solution was placed in a 10-liter glass vessel and 10 carps were liberated therein. After 48 hours, the dead and alive were examined to calculate $TLm_{48}$ (ppm).

TABLE 7

| Test pesticide | $TLm_{48}$ (ppm) |
| --- | --- |
| Dust (3) | >5 |
| Dust (6) | >5 |
| Dust (7) | >5 |
| Dust (11) | >5 |
| Dust (12) | >5 |
| Compound of the formula (I) [dl(acid moiety)-trans isomer: as 0.1% dust | >5 |
| Diazinon: as 0.3% dust | >5 |
| IBP: as 0.3% dust | >5 |
| NAC: as 0.3% dust | >5 |
| PHC: as 0.3% dust | >5 |
| MIPC: as 0.3% dust | >5 |

Experimental example 7

A 1:1 mixture of the compound of the formula (I) and Sumithion or NAC was dissolved or suspended in a corn oil, and the resulting test solution was orally administered to a male mouse at a rate of 0.1 ml/10 g body weight. After 24 hours, the mortality was examined to obtain the median lethal dose ($LD_{50}$ mg/kg).

TABLE 8

| Test pesticide | LD$_{50}$ (mg/kg) |
| --- | --- |
| Compound of the formula (I) [dl(acid moiety)-trans isomer] + Sumithion | >1,000 |
| Compound of the formula (I) [dl(acid moiety)-cis, trans isomer (cis/trans = 23/77)] + Sumithion | >1,000 |
| Compound of the formula (I) [dl(acid moiety)-trans isomer] + NAC | >500 |
| Compound of the formula (I) [dl(acid moiety)-cis, trans isomer (cis/trans = 23/77 ] + NAC | >500 |
| Compound of the formula (I) [dl(acid moiety)-trans isomer] | >2,000 |
| Compound of the formula (I) [dl(acid moiety)-cis, trans isomer (cis/trans = 23/77)] | >2,000 |
| Sumithion | >1,000 |
| NAC | >300 |

Experimental example 8

Soil was placed in a plastic box [5 m×5 m×2 m] to a level of 50 cm from the bottom, and rice plants of about 50 cm high were transplanted at intervals of 50 cm.

Water was then placed in the box so that water depth was 5 cm, and 20 killifishes (*Oryzias latipes*) were released therein. Thereafter, the dusts (1), (4), (11), (13) or (17) prepared in Preparation example 2 were each applied thereto at a rate of 3 kg/10 are. The dust fell on the rice plants as well as on the water surface.

One hour after treatment, 100 green rice leafhopper adults (*Nephotettix cincticeps*) were released in the box which was then immediately covered with a net. After 48 hours, no alive green rice leafhoppers were found, whereas all the killifishes were alive.

What is claimed is:

1. An insecticidal or acaricidal composition comprising an inert pesticide carrier and, as an active ingredient, an insecticidally or acaricidally effective amount of a mixture comprising (I) m-(p-bromophenoxy)-α-cyanobenzyl trans- or trans-cis-2,2-dimethyl-3-(2,2-dichlorovinyl)cyclopropanecarboxylate wherein the trans/cis ratio is not less than 25/75, and an organophosphate of the general formula (II),

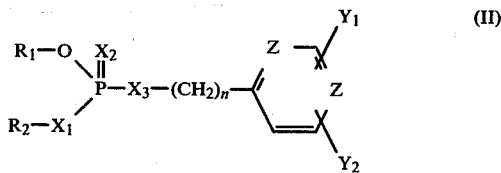

wherein each of R$_1$ and R$_2$ is a C$_1$–C$_3$ alkyl group, each of X$_1$, X$_2$ and X$_3$ is an oxygen or sulfur atom, each of Y$_1$ and Y$_2$ is the same or different C$_1$–C$_3$ alkyl, methylmercapto, cyano or nitro group, or a halogen atom, Z is a carbon or nitrogen atom and n is 0 or 1, wherein the mixing ratio of the compound (I) to the compound (II) is within a range of from 1:1 to 1:100 by weight.

2. An insecticidal or acaricidal composition according to claim 1, wherein the compound (II) is O,O-dimethyl O-(3-methyl-4-nitrophenyl)phosphorothioate.

3. An insecticidal or acaricidal composition according to claim 1, wherein the compound (II) is O,O-dimethyl O-[3-methyl-4-(methylthio)phenyl]thiophosphate.

4. An insecticidal or acaricidal composition according to claim 1, wherein the compound (II) is O,O-diethyl O-(2-isopropyl-4-methyl-6-pyrimidinyl)phosphorothioate.

5. An insecticidal or acaricidal composition according to claim 1, wherein the compound (II) is O,O-dimethyl O-4-cyanophenyl phosphorothioate.

6. An insecticidal or acaricidal composition according to claim 1, wherein the compound (II) is O,O-di-n-propyl p-methylthiophenyl phosphate.

7. An insecticidal or acaricidal composition according to claim 1, wherein the compound (II) is O,O-diisopropyl S-benzyl phosphorothiolate.

8. An insecticidal or acaricidal composition according to claim 1, wherein the compound (II) is O,O-dimethyl O-(3-methyl-4-nitrophenyl)phosphorothionate.

* * * * *